US011285261B2

(12) United States Patent
Mansour et al.

(10) Patent No.: US 11,285,261 B2
(45) Date of Patent: Mar. 29, 2022

(54) SYRINGE ADAPTER

(71) Applicant: Becton, Dickinson and Company, Franklin Lakes, NJ (US)

(72) Inventors: George Mansour, Diamond Bar, CA (US); Linda Ewing, San Clemente, CA (US); Eugene Mason, La Habra Heights, CA (US); Tomas Frausto, Walnut, CA (US); Ryan Callahan, Long Beach, CA (US)

(73) Assignee: CAREFUSION 303, INC., San Diego, CA (US)

( * ) Notice: Subject to any disclaimer, the term of this patent is extended or adjusted under 35 U.S.C. 154(b) by 367 days.

(21) Appl. No.: 16/158,179

(22) Filed: Oct. 11, 2018

(65) Prior Publication Data
US 2020/0114071 A1   Apr. 16, 2020

(51) Int. Cl.
*A61M 5/162* (2006.01)
*A61M 39/12* (2006.01)
*A61J 1/20* (2006.01)
*A61M 39/10* (2006.01)

(52) U.S. Cl.
CPC ............ *A61M 5/162* (2013.01); *A61J 1/2065* (2015.05); *A61M 39/12* (2013.01); *A61M 2039/1072* (2013.01); *A61M 2039/1077* (2013.01)

(58) Field of Classification Search
CPC ...... A61M 39/12; A61M 39/22; A61M 39/26; A61M 39/105; A61M 2039/1066; A61M 2039/1072; A61M 2039/1077; A61M 2039/2433; A61M 2039/263; A61M 2039/1044; A61M 2039/268; A61M 5/385; A61M 2005/1402; A61M 2005/1404; A61J 1/2065

See application file for complete search history.

(56) References Cited

U.S. PATENT DOCUMENTS

| 4,623,343 A | 11/1986 | Thompson |
| 8,647,310 B2 * | 2/2014 | Fangrow, Jr .......... A61M 39/26 604/236 |
| 2004/0138626 A1 * | 7/2004 | Cote, Sr. ............... A61M 39/26 604/249 |

(Continued)

OTHER PUBLICATIONS

Invitation to Pay Additional Fees, Partial Search Report, and Provisional Opinion for International Patent Application No. PCT/US2019/054098, dated Jan. 15, 2020, 12 pages.

(Continued)

*Primary Examiner* — Nathan R Price
*Assistant Examiner* — Justin L Zamory
(74) *Attorney, Agent, or Firm* — Morgan, Lewis & Bockius LLP

(57) ABSTRACT

An exemplary syringe adapter for coupling with a syringe may include a housing. A needle-free connector may be disposed in the housing. A communication member may be in slidable engagement with the housing. The communication member may be slidable, with respect to the housing, between an unactuated state and an actuated state of the syringe adapter. A cannula may extend from the communication member. In the unactuated state, the cannula may be retracted within the needle-free connector. In the actuated state, the cannula may protrude through and axially beyond the needle-free connector.

9 Claims, 14 Drawing Sheets

(56) References Cited

U.S. PATENT DOCUMENTS

2006/0142735 A1\* 6/2006 Whitley ................ A61M 39/26
                                                               604/537
2016/0030293 A1   2/2016 Dorsey et al.
2016/0250413 A1   9/2016 Good et al.

OTHER PUBLICATIONS

International Search Report and Written Opinion for Application No. PCT/US2019/054098, dated Mar. 17, 2020, 17 pages.

\* cited by examiner

SYRINGE ADAPTER

BACKGROUND

The present disclosure relates generally to medical connectors used in fluid transfer applications. More particularly, the present disclosure relates to a syringe adapter for the transfer of fluids in medical settings.

Medical connectors are widely used to transmit, prepare, and deliver medical fluids. The delivery of a medical fluid may include administering the medical fluid intravenously through an intravenous (IV) set from a fluid source such as a syringe.

Unlike other fluid sources, such as collapsible bags, the fluid-filled syringe includes a rigid structure and cannot collapse when the plunger of the syringe is stationary and the fluid is being pulled from the syringe. As a result, ambient air needs to be introduced into the syringe to replace the fluid that is being pulled from the syringe. A traditional approach to allow air to enter the syringe, as fluid is being pulled from the syringe, includes attaching a device between the syringe and the IV set. For example, the device conventionally includes an open female Luer with a cannula that protrudes past the female Luer. The cannula is inserted into the syringe, such that a filter at the other end of the cannula provides an air path into the syringe through the cannula. When the syringe is empty and needs to be removed and replaced with another syringe, however, the female Luer will be exposed to the atmosphere, due to the cannula protruding past the female Luer, creating an open system during syringe changes.

SUMMARY

An aspect of the present disclosure provides a syringe adapter for coupling with a syringe. The syringe adapter comprises a housing and a needle-free connector disposed in the housing. A communication member is in slidable engagement with the housing. The communication member is slidable, with respect to the housing, between an unactuated state and an actuated state of the syringe adapter. A cannula extends from the communication member. In the unactuated, the cannula is retracted within the needle-free connector. In the actuated state, the cannula protrudes through and axially beyond the needle-free connector.

In some aspects, a piston element is disposed in the needle-free connector. The piston element comprises a piston head and a sealable orifice disposed through the piston head, wherein the sealable orifice is in a sealed state when the piston element is in an uncompressed state and is in an opened state when the piston element is in a compressed state.

In some aspects, the needle-free connector comprises a connection port sealingly flush with the piston head and the sealable orifice when the syringe adapter is uncoupled with the syringe.

In some aspects, a conduit extends from, and is disposed through, the communication member, wherein the conduit is fluidly separated from the needle-free connector when the syringe adapter is coupled with the syringe and in the unactuated state.

In some aspects, the conduit is in fluid communication with the needle-free connector when the syringe adapter is coupled with the syringe and in the actuated state.

In some aspects, a duct extends from, and through, the communication member, wherein the duct fluidly couples the cannula to at least one vent disposed in a filter housing.

In some aspects, a filter is disposed in the filter housing and a valve is disposed between the filter and the cannula, wherein the valve is configured to allow fluid to flow from the at least one vent through the filter to the cannula and is configured to prevent fluid flow from the cannula to the filter.

In some aspects, a first fluid path and a second fluid path is provided when the syringe adapter is coupled to the syringe and in the actuated state.

In some aspects, the first fluid path is configured to provide filtered ambient air into the syringe and the second fluid path is configured to allow fluid from the syringe to flow to an intravenous set coupled to the syringe adapter.

In some aspects, the first fluid path flows through at least the cannula, the duct, and the at least one vent.

In some aspects, the second fluid path flows through at least the connection port, the piston element, and the conduit.

Some other aspects of the present disclosure provide a syringe adapter for coupling a syringe to a fluid system. The syringe adapter comprises a female connector. A body is in fluid communication with the female connector. A male connector is in fluid communication with the female connector and the body. The male connector is configured to couple with a medical device. A cannula extends axially through the body and out through the female connector. A filter housing is in fluid communication with the cannula. The filter housing is elevated axially beyond the female connector, wherein a first fluid path is formed through the filter housing and the cannula and a second fluid path is formed through the female connector, the body, and the male connector. The filter housing is configured to prevent a filter disposed in the filter housing from contacting fluid in the first fluid path and a closed system is provided when the male connector is uncoupled from the medical device.

In some aspects, a flexible tubing fluidly couples the filter housing to the cannula.

In some aspects, the female connector is coupled to the syringe such that the cannula is arranged within a chamber of the syringe.

In some aspects, a clip is arranged around the syringe and the flexible tubing. The clip is configured to secure the flexible tubing to the syringe.

In some aspects, the medical device is an intravenous set. In further aspects, the medical device is a needle-free connector.

Some other aspects of the present disclosure provide a syringe adapter for coupling with a syringe. The syringe adapter comprises a female connector configured to couple with the syringe. A body is in fluid communication with the female connector. A male connector is in fluid communication with the female connector and the body. The male connector is configured to couple with a medical device. A chamber extends from, and is in fluid communication with, the body, wherein the chamber is configured to receive fluid from the syringe for subsequent delivery to the medical device. A needle-free connector is disposed at, and in fluid communication with, the female connector, wherein the needle-free connector is configured to provide a closed system when the female connector is uncoupled from the syringe.

In some aspects, a valve is disposed between the female connector and the needle-free connector.

In some aspects, the chamber is one of a resilient bag, a non-resilient bag, and a collapsible plastic container.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

The various embodiments of a syringe adapter illustrated in FIGS. 1-17 are configured to couple with a fluid source and provide a closed system, including a closed sealed surface, during a fluid source change from an IV set. In certain embodiments, in addition to including a closed sealed surface during fluid source changes from the IV set, the syringe adapter also includes a cannula in fluid communication with an air vent to allow filtered air to enter the fluid source as fluid is pulled out of the fluid source. In such embodiments, the syringe adapter is configured to prevent fluid in the fluid source from contacting a filter disposed in the air vent.

Figure 1:
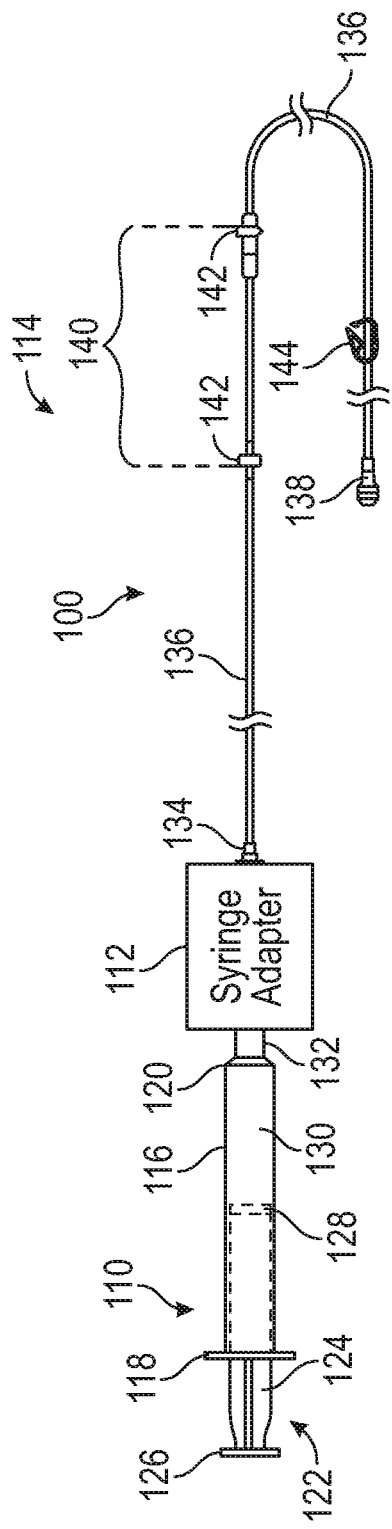
FIG. 1 illustrates a schematic view of fluid delivery system in accordance with aspects of the present disclosure.

FIG. 1 illustrates an exemplary fluid delivery system 100. The fluid delivery system 100 includes a syringe 110, a syringe adapter 112, and an intravenous (IV) set 114. The fluid delivery system 100 is an exemplary system in which the syringe adapter 112 is utilized and it is understood that the syringe adapter 112 may be used in other fluid delivery systems. The syringe 110 includes a syringe barrel 116, a collar 118 extending radially outwardly from the syringe barrel 116 at one end of the syringe barrel 116, and an end wall 120 formed at an opposite end of the syringe barrel 116. The syringe 110 also includes a plunger 122. The plunger 122 includes a body 124, a thumb press 126 attached to one end of the body 124, and a stopper 128 (shown in phantom) attached to an opposite end of the body 124. The syringe barrel 116 slidably receives the stopper 128 and the body 124 of the plunger 122, such that a syringe chamber 130 is formed within the syringe barrel 116 between the stopper 128 and the end wall 120 of the syringe barrel 116. A tip 132 extends axially outwardly from the end wall 120 and is in fluid communication with the syringe chamber 130. In some aspects, the tip 132 is a male Luer connector.

The syringe adapter 112 is configured to matingly couple with the tip 132. The syringe adapter 112 is also configured to matingly couple with a connector 134 of the IV set 114. The IV set 114 includes tubing 136 connected to a fitting 138. For example, the fitting 138 is a needle-free Luer connector suitable for connection to an infusion device (not shown), such as an IV needle. In some aspects, a pumping segment 140, which is a section of tubing suitable for peristaltic manipulation to cause fluid to flow through the tubing and includes alignment fittings 142 to facilitate proper placement of the pumping segment 140 in a pump (not shown), connects segments of the tubing 136. The IV set 114 also includes a clamp 144 that can be closed to stop flow through the tubing 136.

FIGS. 2-7 illustrate an embodiment of a syringe adapter 200. In some aspects, the syringe adapter 200 includes a housing 210 slidably engaged with a communication member 212. The housing 210 includes a connection port 214 disposed at one end of the housing 210 and a receiving opening 216 disposed at the other end of the housing 210. A female connector 218 forms part of the housing 210 adjacent the connection port 214. The female connector is configured to couple with male connectors on various medical device components. In some aspects, the female connector is a female Luer connector configured to couple with male Luer connectors on various medical device components. The housing 210 also includes a needle-free connector section 220 and a receiving section 222, such that the needle-free connector section 220 is disposed between the connection port 214 and the receiving section 222. The receiving section 222 is disposed between the needle-free connector section 220 and the receiving opening 216.

A needle-free connector 224 is disposed at the needle-free connector section 220 of the housing 210. The needle-free connector 224 includes the connection port 214 and the female connector 218. The needle-free connector 224 also includes a hollow cylinder 226 disposed within the needle-free connector section 220 of the housing 210. The hollow cylinder 226 includes a head 228 at one end and a base 230 at the other end. The head 228 of the hollow cylinder 226 is offset axially inwardly from the connection port 214 within the needle-free connector section 220 of the housing 210, such that a bore 232 extends from the connection port 214 to the head 228. The connection port 214, the bore 232, and the hollow cylinder 226 are all coaxially aligned.

Figure 2:
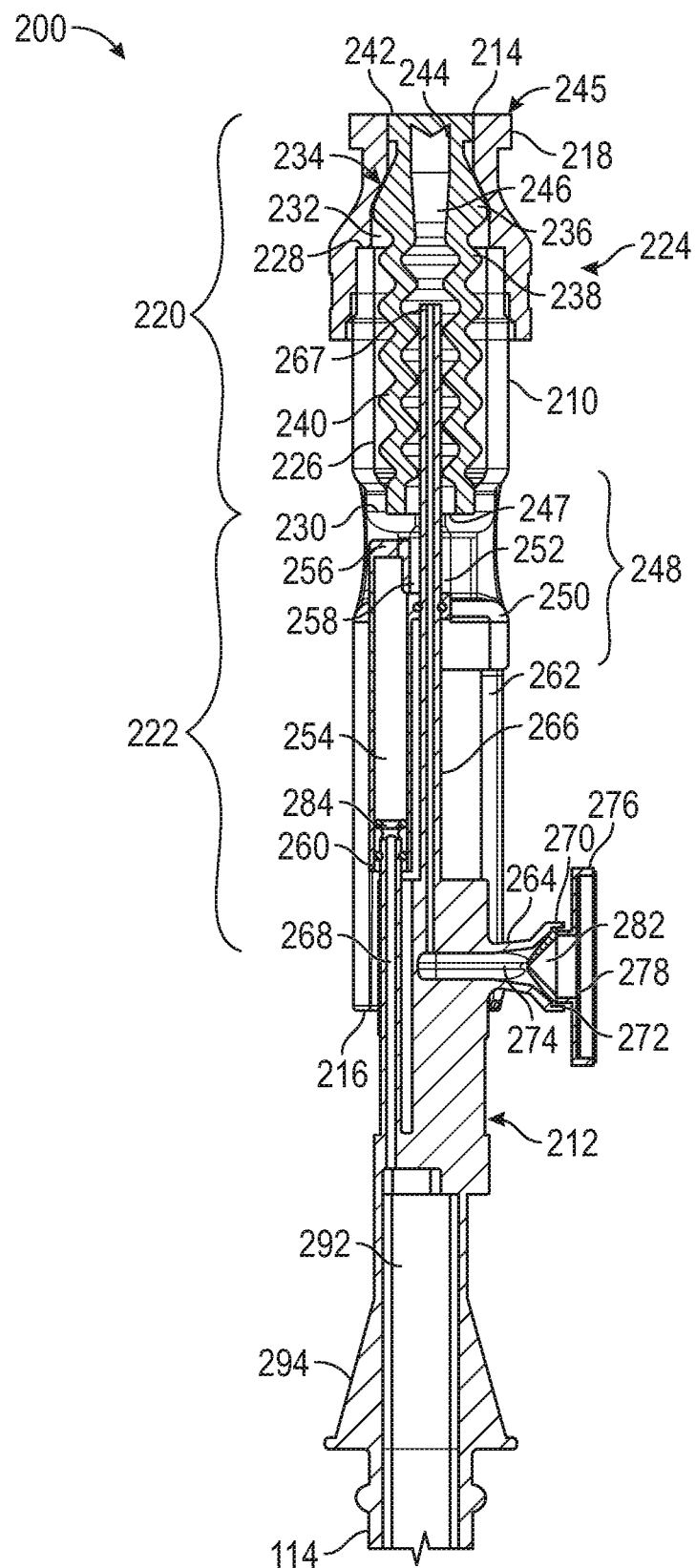
FIG. 2 illustrates a side view of a syringe adapter depicted in an uncoupled, unactuated state, with portions sectioned and broken away to show details, in accordance with aspects of the present disclosure.
Figure 3:
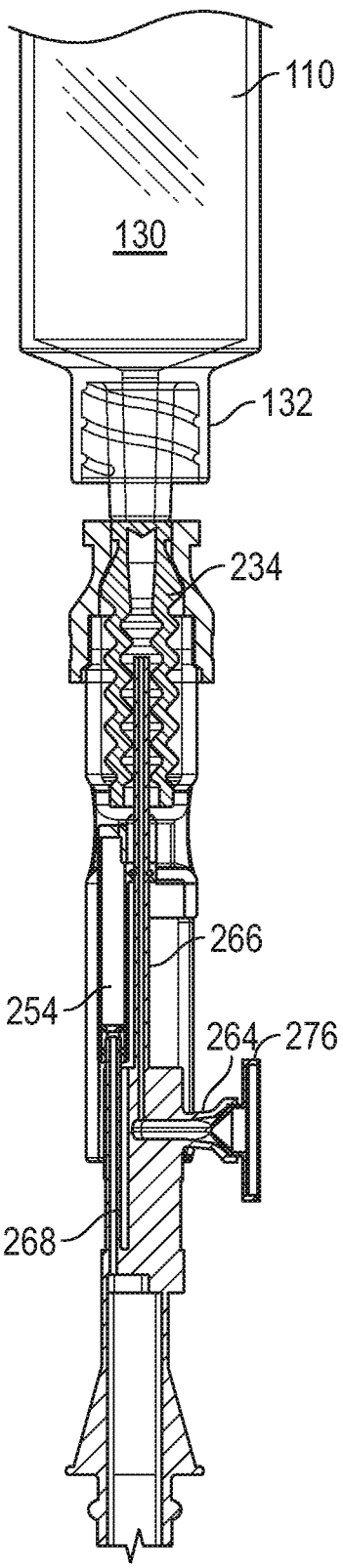
FIG. 3 illustrates a side view of the syringe adapter of FIG. 2 depicted in the uncoupled, unactuated state with a syringe in close proximity, but uncoupled to the syringe adapter, in accordance with aspects of the present disclosure.

The needle-free connector 224 also includes a resiliently deformable piston element 234. In an uncoupled, unactuated state of the syringe adapter 200 shown in FIG. 2, the resiliently deformable piston element 234 is captured between the connection port 214 and the base 230. The piston element 234 includes a piston 236 and a compressible member 238 formed to the piston 236. In some aspects, the compressible member 238 includes a plurality of bellows 240. The piston 236 includes a piston head 242. The piston head 242 includes a sealable orifice 244 disposed therethrough, which is in a sealed state when the piston element 234 is uncompressed and is in an opened state when the piston element 234 in compressed. In the uncoupled, unactuated state of the syringe adapter 200, as depicted in FIGS. 2 and 3, the piston element 234 is uncompressed with the sealable orifice 244 in a sealed state, such that the compressible member 238 is urged against the base 230 while the piston head 242 is located internally to the housing 210 within the bore 232 and is sealingly flush with the surrounding connection port 214 collectively forming a flat, closed, and swabable surface 245. Moreover, the piston element 234 is hollow and includes a piston passage 246, which extends from an exit orifice 247 of the compressible member 238 to the sealable orifice 244.

The receiving section 222 includes a transition section 248 disposed adjacent to the needle-free connector section 220. The transition section 248 includes an annular shoulder 250 axially offset from the base 230, such that a chamber 252 is formed between the base 230 and the shoulder 250. The chamber 252 is fluidly coupled to the piston passage 246 via the exit orifice 247 and is coaxially aligned with an aperture 253 disposed in the shoulder 250. A channel 254 is disposed in the receiving section 222 and includes a closed end 256, which is disposed adjacent the chamber 252 in the transition section 248. The channel 254 includes a transfer passage 258 disposed proximate the closed end 256. The channel 254 is fluidly coupled to the chamber 252 via the transfer passage 258. The channel 254 extends axially from the closed end 256 through the shoulder 250 to an opened end 260. The opened end 260 of the channel 254 terminates within the receiving section 222 and is axially offset from the receiving opening 216 of the housing 210. The receiving section 222 also includes a slot 262 that extends axially between the shoulder 250 and the receiving opening 216. The slot 262 is configured to slidably guide a neck 264 of the communication member 212 when the syringe adapter 200 transitions from a coupled, unactuated state to a coupled, actuated state.

Figure 6:
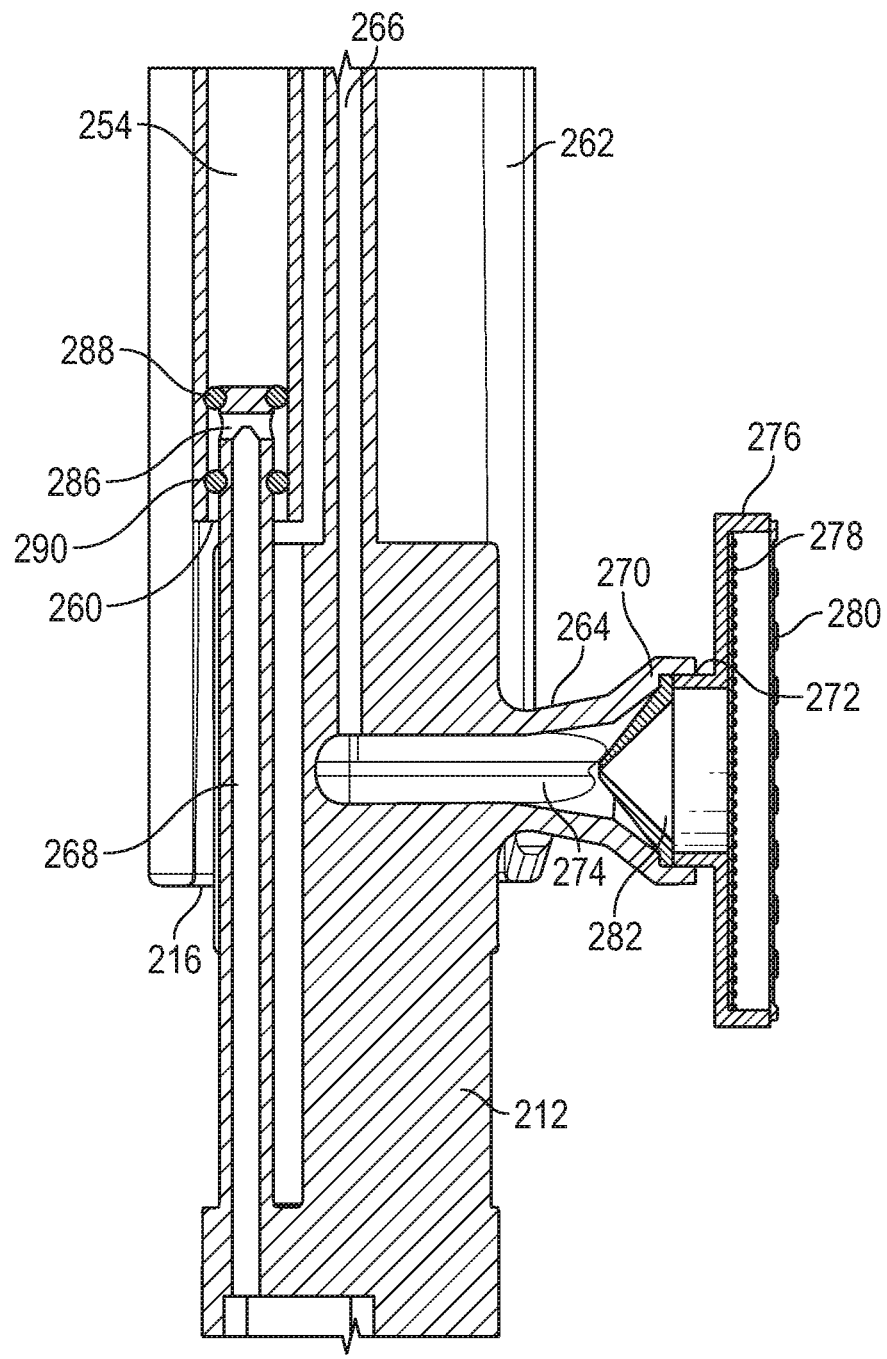
FIG. 6 illustrates a detail side view of the syringe adapter of FIG. 4, in accordance with aspects of the present disclosure.
Figure 7:
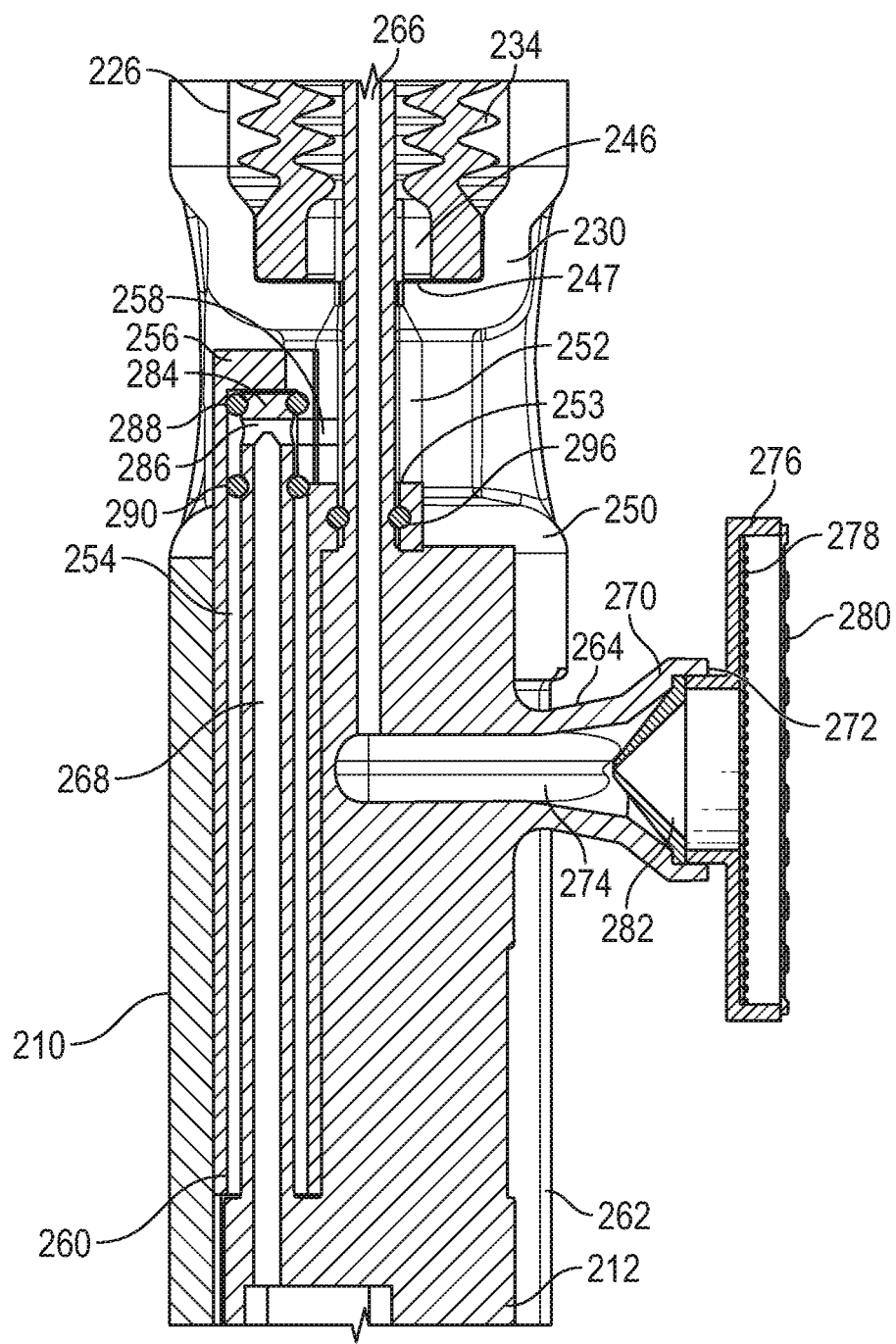
FIG. 7 illustrates a detail side view of the syringe adapter of FIG. 5, in accordance with aspects of the present disclosure.
Figure 9:
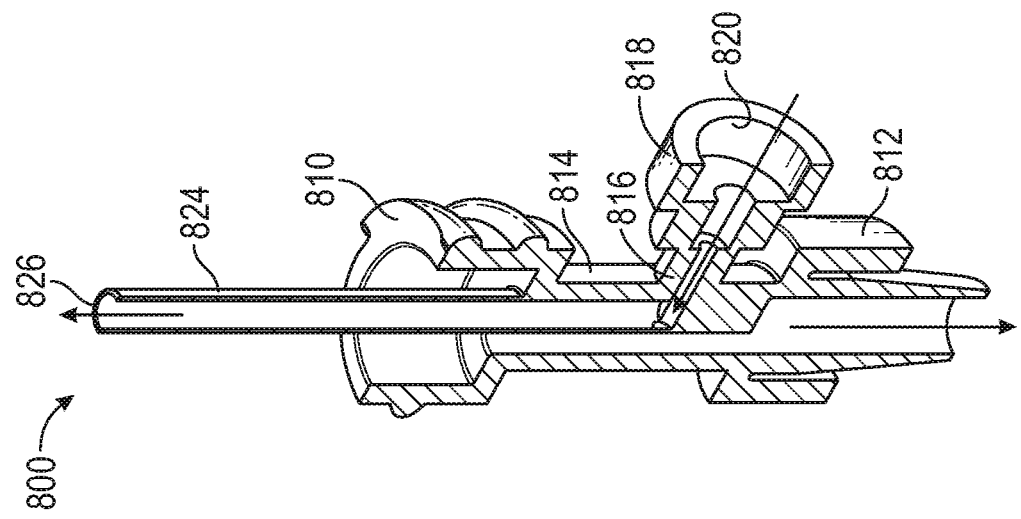
FIG. 9 illustrates a cross-sectional perspective view of the syringe adapter of FIG. 8, in accordance with aspects of the present disclosure.
Figure 8:
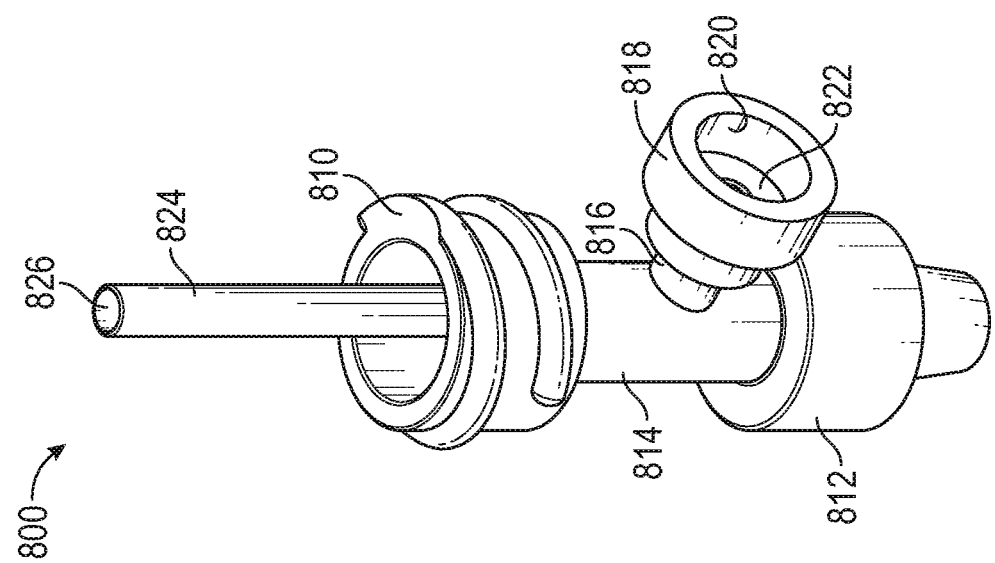
FIG. 8 illustrates a perspective view of an alternative embodiment of a syringe adapter, in accordance with aspects of the present disclosure.
Figure 10:
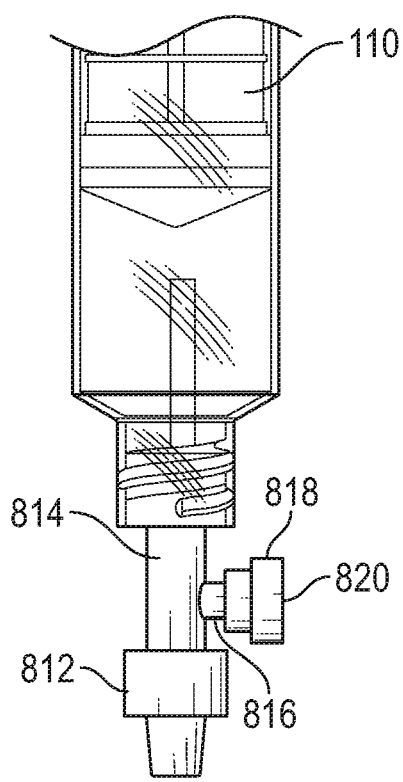
FIG. 10 illustrates a side view of the syringe adapter of FIG. 8 attached to a syringe, in accordance with aspects of the present disclosure.
Figure 11:
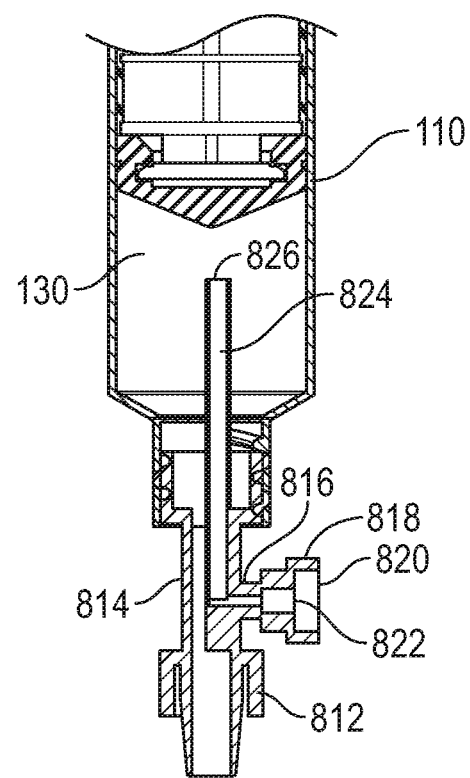
FIG. 11 illustrates a cross-sectional side view of the syringe adapter attached to the syringe in FIG. 10, in accordance with aspects of the present disclosure.
Figure 12:
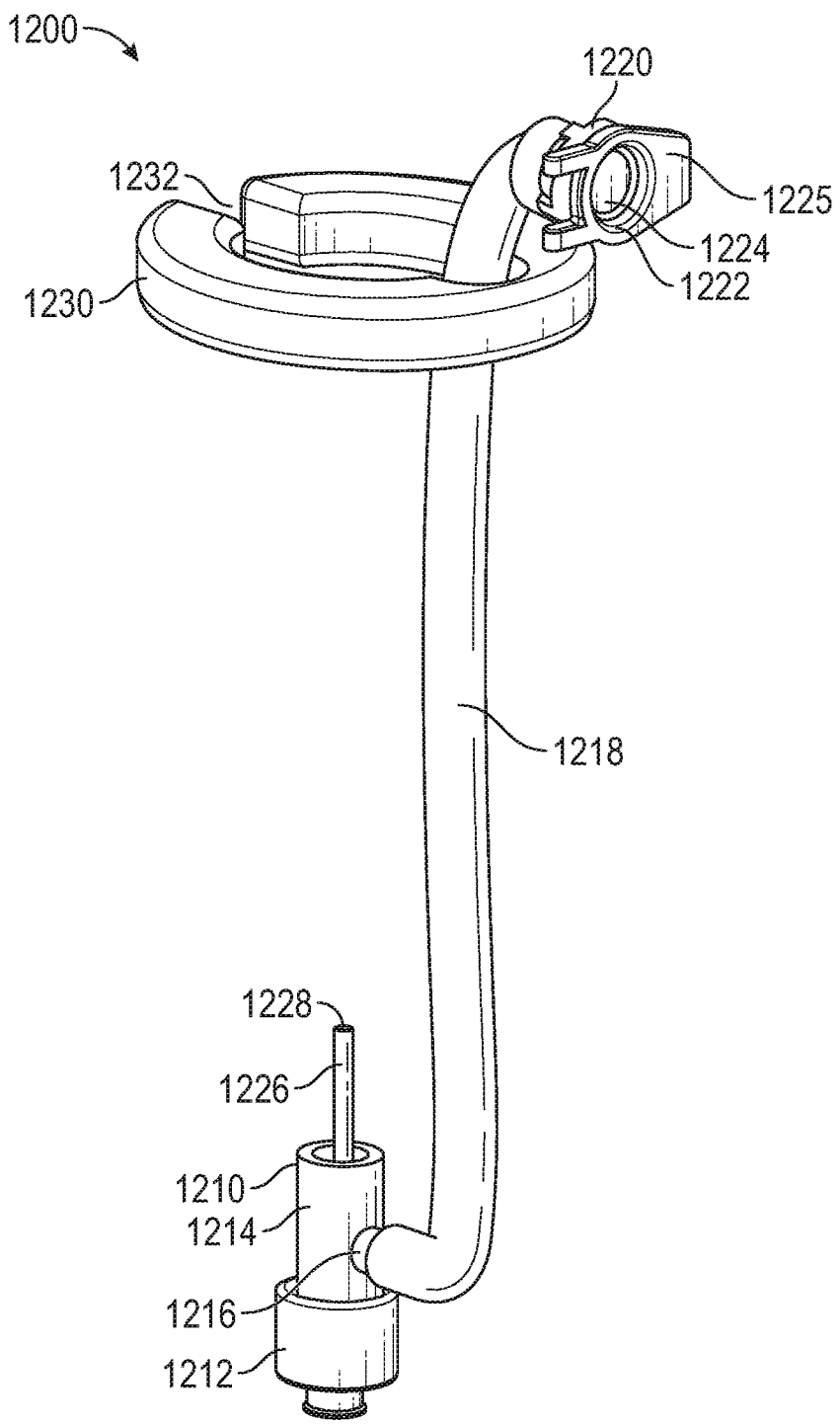
FIG. 12 illustrates a perspective view of another alternative embodiment of a syringe adapter, in accordance with aspects of the present disclosure.
Figure 13:
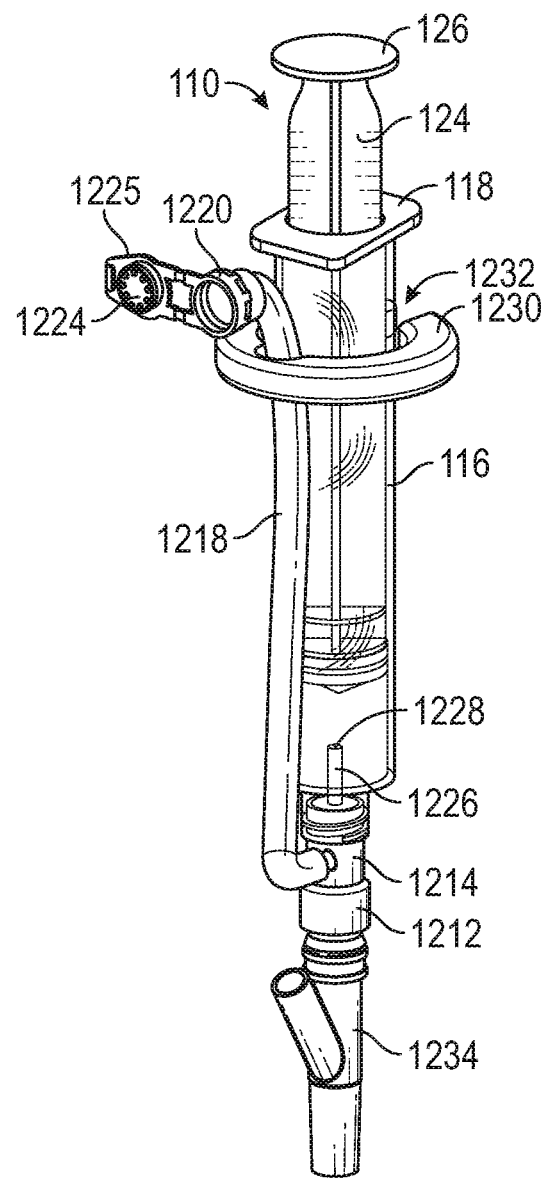
FIG. 13 illustrates a perspective view of the syringe adapter of FIG. 12 attached to a syringe, in accordance with aspects of the present disclosure.
Figure 14:
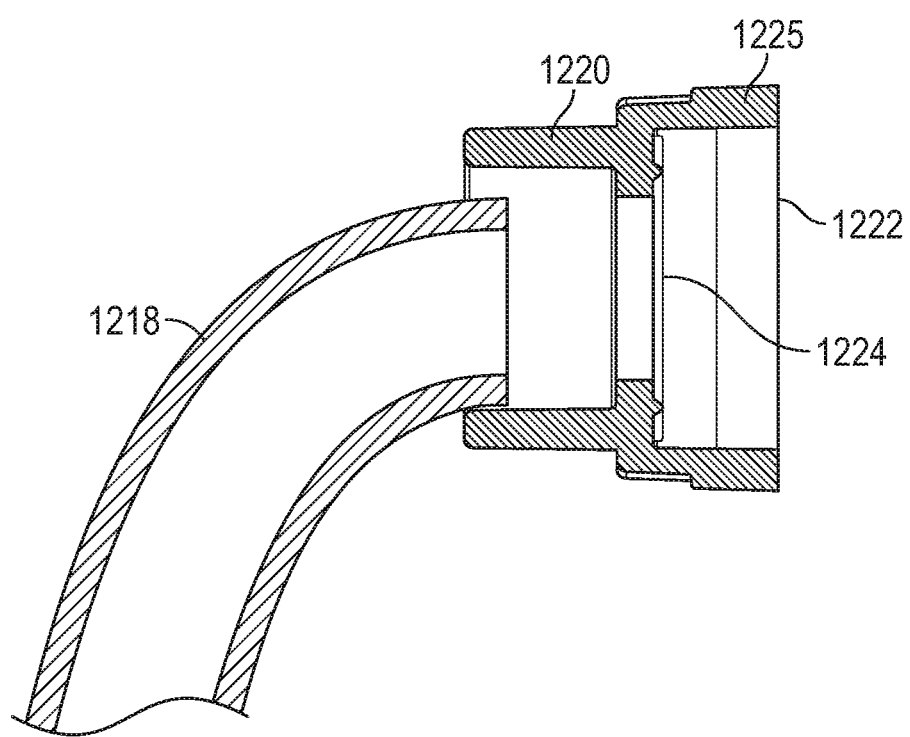
FIG. 14 illustrates a cross-sectional view of an air vent of the syringe adapter in FIG. 12, in accordance with aspects of the present disclosure.
Figure 15:
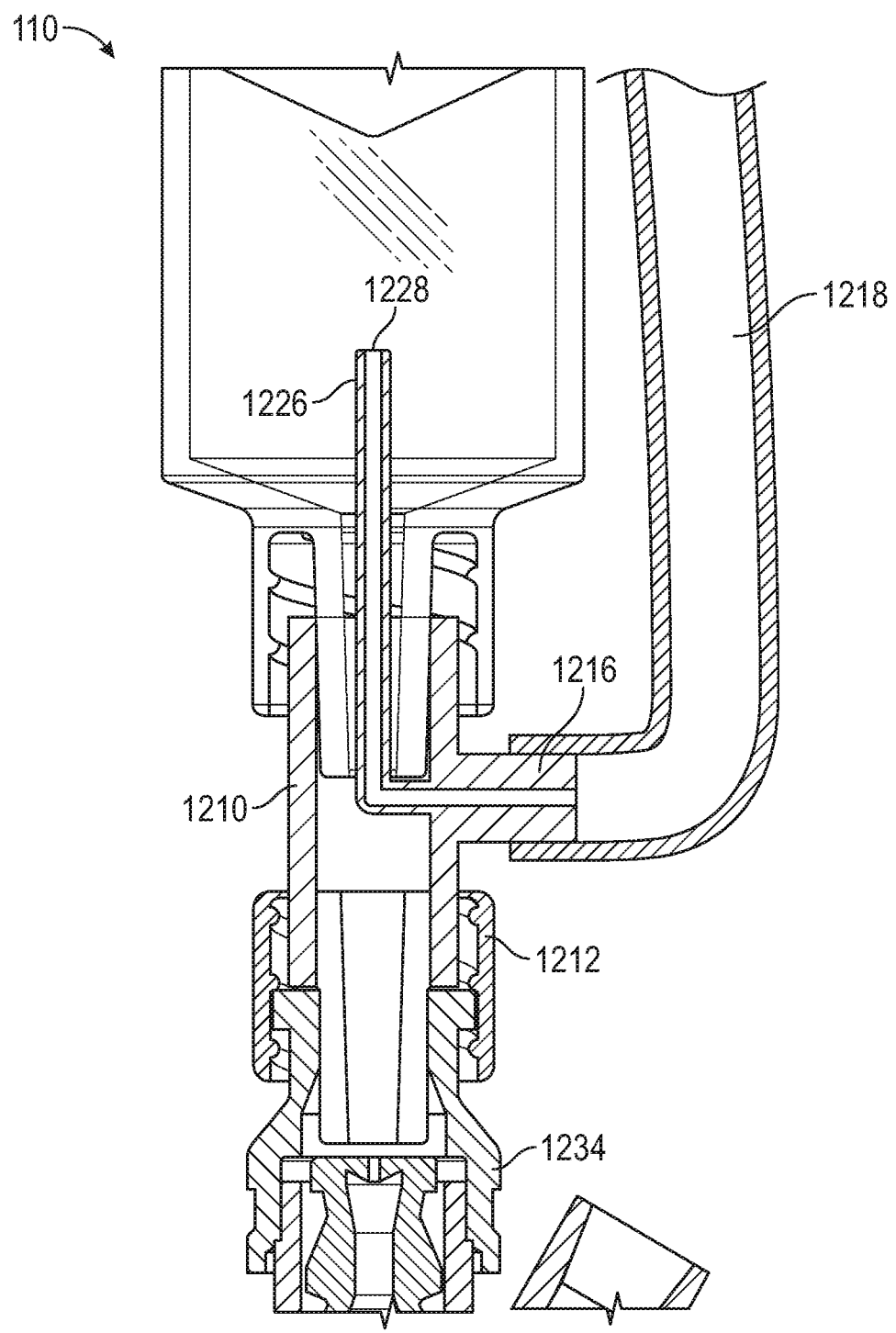
FIG. 15 illustrates a detail side view of the syringe adapter of FIG. 12 attached to the syringe, with portions sectioned and broken away to show internal fluid paths, in accordance with aspects of the present disclosure.

With particular reference to FIGS. 2 and 6-7, the communication member 212 includes the neck 264, a cannula 266, and a conduit 268. The neck 264 extends radially from the communication member 212 and terminates at a valve housing 270 that includes an inlet port 272. A duct 274 is disposed within the communication member 212 through the neck 264 and the valve housing 270 to the inlet port 272. A filter housing 276 is received in fluid communication by the inlet port 272. The filter housing 276 surrounds a filter 278 and includes at least one vent 280 configured to allow ambient air to pass through the filter 278. A valve 282 is disposed in the valve housing 270 and is configured to allow fluid to flow from the at least one vent 280 through the filter 278 and into the duct 274 and prevent fluid to flow in the opposite direction from the duct 274 to the filter housing 276 ensuring that the filter 278 will not get wetted from fluid possibly in the duct 274.

The cannula 266 extends axially from, and through, the communication member 212 and is fluidly coupled to the duct 274 at one end and terminates at an opening 267 at an opposite end. The conduit 268 is radially offset from the cannula 266 and extends axially from, and through, the communication member 212. Externally of the communication member 212, a crown 284 is disposed at the end of the conduit 268, such that the conduit 268 terminates axially at the crown 284 to fluidly couple with a passage 286. A first O-ring 288 is disposed around the crown 284 and a second O-ring 290 is disposed around the conduit 268 between the passage 286 and the communication member 212. Internally of the communication member 212, the conduit 268 is fluidly coupled to an exit port 292. A connector 294 is disposed around the exit port 292 and is configured to couple with various medical devices, such as, for example, the connector 134 of the IV set 114.

Upon assembly of the syringe adapter 200, the communication member 212 is received, in slidable engagement, by the receiving opening 216 of the housing 210, such that the conduit 268 is slidably received by the channel 254, the cannula 266 is slidably received by a third O-ring 296 disposed in the aperture 253, and the neck 264 is slidably received by the slot 262. The third O-ring 296 is configured to seal the cannula 266 with respect to the aperture 253 while allowing the cannula 266 to sealably slide along within the O-ring 296.

FIG. 3 illustrates the syringe adapter 200 coupled to an IV set, such as, for example, the IV set 114 and in an uncoupled, unactuated state. A pre-filled syringe, such as, for example, the syringe 110 is in close proximity to, and prepared for coupling with, the syringe adapter 200. In the uncoupled, unactuated state, the cannula 266 is retracted into the needle-free connector 224. For example, the piston element 234 is uncompressed, such that the opening 267 of the cannula 266 is arranged in the piston passage 246 within the compressible member 238, the neck 264 rests in the slot 262 proximate the receiving opening 216, and the conduit 268 is arranged in the channel 254 proximate the opened end 260, such that the passage 286 is unaligned with the transfer passage 258 and the conduit 268 is fluidly separated from the needle-free connector 224. Moreover, the sealable orifice 244 is in the sealed state with the piston head 242 sealingly flush with the surrounding connection port 214 forming the flat, closed, and swab able surface 245.

Figure 4:
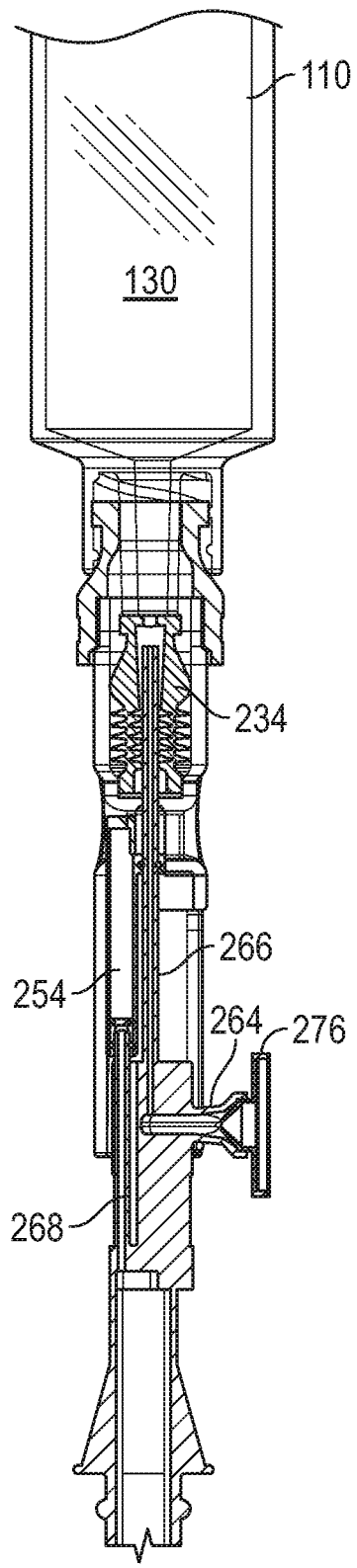
FIG. 4 illustrates a side view of the syringe adapter of FIG. 2 depicted in a coupled, unactuated state with the syringe coupled to the syringe adapter, in accordance with aspects of the present disclosure.

FIG. 4 illustrates the syringe adapter 200 in a coupled, unactuated state with the syringe 110. With the syringe 110 coupled to the syringe adapter 200, the male Luer tip 132 is in contact with the piston head 242 and compresses the piston element 234 to move the sealable orifice 244 from the sealed state to the opened state. In the coupled, unactuated state, the neck 264 and the conduit 268 are arranged similarly as in the uncoupled, unactuated state, but with the piston element 234 in the compressed state, the opening 267 of the cannula 266 is now arranged in the piston passage 246 within the piston 236 instead of the compressible member 238. As the passage 286 and the transfer passage 258 are unaligned in this state and with the first O-ring 288 in sealing contact with the channel 254, ambient air from the filter housing 276 is prevented from flowing through the channel 254 and past the first O-ring 288 to the IV set 114 via the exit port 292. This is especially beneficial in scenarios where the IV set 114 includes the pumping segment 140 inserted into a pump and the pump is turned on before the syringe adapter 200 transitions to the coupled, actuated state. Moreover, if the plunger 122 is accidentally depressed in this state, the valve 282 prevents fluid from the syringe chamber 130 from flowing to the filter 278.

Figure 5:
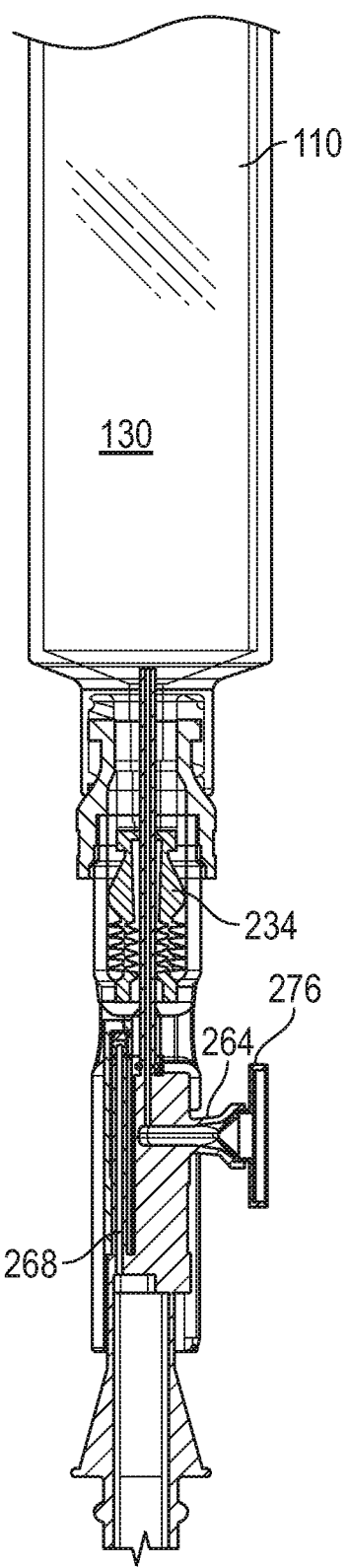
FIG. 5 illustrates a side view of the syringe adapter of FIG. 2 depicted in a coupled, actuated state with the syringe coupled to the syringe adapter, in accordance with aspects of the present disclosure.

In order to allow fluid to flow from the syringe 110 to the IV set 114, the syringe adapter 200 is required to enter the coupled, actuated state, as illustrated in FIG. 5. For the syringe adapter 200 to enter the coupled, actuated state from the coupled, unactuated state, the housing 210 is slid axially around, and locked to, the communication member 212, such that the cannula 266 is protruded from the needle-free connector 224. For example, the neck 264 is arranged in the slot 262 proximate the shoulder 250, the communication member 212 abuts the shoulder 250, the conduit 268 is arranged in the channel 254 with the crown 284 abutting the closed end 256 of the channel 254, and the opening 267 of the cannula 266 is arranged in the syringe 110 axially beyond the end wall 120 at a location that is axially beyond a fluid intake at the needle-free connector 224. With the crown 284 abutting the closed end 256 of the channel 254, the passage 286 aligns with the transfer passage 258 to fluidly couple the conduit 268 with the chamber 252 and to the needle-free connector 224. The second O-ring 290 seals the conduit 268 with the channel 254 and prevents fluid entering the passage 286 from traveling axially past the second O-ring 290 into the channel 254.

When the syringe adapter 200 is in the coupled, actuated state a first fluid path is formed, at least, through the at least one vent 280, the duct 274, and the cannula 266. For example, ambient air enters the first fluid path through the at least one vent 280, the filter 278, the valve 282, the duct 274, the cannula 266, and the opening 267 of the cannula 266 into the syringe chamber 130. As the first fluid path provides filtered ambient air into the syringe chamber 130, a reservoir is created in the syringe chamber 130 allowing the fluid in the syringe chamber 130 to vent or flow through a second fluid path without requiring the plunger 122 to be depressed. The second fluid path is formed, at least, through the connection port 214, the conduit 268, and the exit port 294. For example, fluid from the syringe chamber 130 flows through the tip 132 and the around the cannula 266 following the second fluid path at the connection port 214 through the bore 232, the sealed orifice 244 in the opened state, the piston passage 246, the exit orifice 247, the chamber 252, the transfer passage 258, the passage 286, the conduit 268, and the exit port 294 to the IV set 114. In some aspects, the fluid in the syringe chamber 130 flows through the second fluid path by gravity. In other aspects in which the IV set 114 includes the pumping segment 140, a bag pump (not shown) is utilized, such that the pumping segment 140 is inserted into the bag pump to regulate peristaltic manipulation causing the fluid to flow through the second fluid path. For example, the syringe adapter 200 can be utilized with the bag pump, such as a large volume pump (LVP), in such a manner that a depleted IV bag can be replaced with the syringe 110 and syringe adapter 200 without necessitating a separate syringe pump.

When the syringe 110 is ready to be replaced the syringe adapter 200 is transitioned from the coupled, actuated state to the coupled, unactuated state by sliding the housing 210 axially with respect to the communication member 212, and then transitioned from the coupled, unactuated state to the uncoupled, unactuated state by uncoupling the syringe 110 from the syringe adapter 200. In the uncoupled, unactuated state, the sealable orifice 244 is in the sealed state and the piston head 242 is located internally to the housing 210 within the bore 232 and is sealingly flush with the surround connection port 214, such that closed, flat surface 245 can be swabbed before coupling a replacement syringe to the syringe adapter 200.

FIGS. 8-11 illustrate another embodiment of a syringe adapter 800. Similar to the syringe adapter 200, the syringe adapter 800 is couplable to a fluid source and includes a first fluid path that allows filtered air to enter the fluid source as fluid is pulled out of the fluid source through a second fluid path while preventing a filter in the first fluid path from exposure to fluid in the fluid source. The syringe adapter 800 also provides a closed system during a fluid source change from an IV set.

The syringe adapter 800 includes a female connector 810, a male connector 812, and a body 814 fluidly coupling the female connector 810 to the male connector 812. In some aspects, the female connector 810 is a female Luer connector and the male connector 812 is a male Luer connector. The syringe adapter 800 also includes a passage 816 extending radially through the body 814. A filter housing 818 is fluidly coupled to an end of the passage 816 that is exterior to the body 814. The filter housing 818 terminates at a vent 820, which is also in fluid communication with the passage 816. A filter 822 is disposed in the filter housing 818 and filters ambient air entering the vent 820. In some aspects, a valve (not shown) is disposed in the filter housing 818 between the filter 822 and the passage 816 and is configured to allow ambient air to flow from the vent 820 to the passage 816 via the filter 822 and to prevent fluid from flowing from the passage 816 to the filter 822. In some aspects, the filter housing 818 is elevated with respect to the female connector 810 and is angled with respect to the passage 816 and extends axially away from the male connector 812 and axially beyond the female connector 810, such that the filter housing 818 and the filter 822 is arranged above (e.g., axially beyond) the female connector 810.

The syringe adapter 800 also includes a cannula 824 fluidly coupled to the passage 816 at an end of the passage 816 that is disposed within the body 814. The cannula 824 extends axially within the body 814 and out through the female connector 810. An opening 826 of the cannula 824 is arranged axially offset from, and exterior to, the female connector 810. A first fluid path is formed through, at least, the cannula 824, the passage 816, and the vent 820. A second fluid path is formed through, at least, the female connector 810, the body 814, and the male connector 812.

The female connector 810 is configured to couple with a male connector of a fluid source, such as, for example, the syringe 110. The male connector 812 is configured to couple with a female connector of a medical device, such as, for example, the IV set 114. In operation, the syringe adapter 800 is coupled to the IV set 114 and the syringe 110 is coupled to the syringe adapter 800, such that the opening 826 of the cannula 824 is arranged within the syringe chamber 130 of the syringe 110. As the first fluid path provides filter ambient air into the syringe chamber 130, a reservoir is created in the syringe chamber 130 allowing the fluid in the syringe chamber 130 to vent through the second fluid path without requiring the plunger 122 to be depressed. Moreover, in aspects where the filter housing 818 is angled with respect to the passage 816 and extends axially away from the male connector 812 and axially beyond the female connector 810, the filter 822 is prevented from coming in contact with the fluid from the syringe chamber 130, if the plunger 122 is accidentally depressed, due to the arrangement of filter housing 818 with respect to fluid intake at the second fluid path. In some aspects, the fluid in the syringe chamber 130 flows through the second fluid path by gravity. In other aspects in which the IV set 114 includes the pumping segment 140, a bag pump (not shown) is utilized, such that the pumping segment 140 is inserted into the bag pump to regulate peristaltic manipulation causing the fluid to flow through the second fluid path.

When the syringe 110 is ready to be replaced the syringe adapter 800, while still coupled to the syringe 110, is uncoupled from the IV set 114 providing a closed system during the syringe change. Both the syringe 110 and the syringe adapter 800 can be disposed and a new syringe adapter 800 can be coupled to the IV set 114 so that a replacement syringe can be coupled to the syringe adapter 800 without having to break the closed system.

FIGS. 12-15 illustrate another embodiment of a syringe adapter 1200. Similar to the syringe adapter 200, the syringe adapter 1200 is couplable to a fluid source and also includes a first fluid path that allows filtered air to enter the fluid source as fluid is pulled out of the fluid source through a second fluid path while preventing a filter in the first fluid path from exposure to fluid in the fluid source. The syringe adapter 1200 also provides a closed system during a fluid source change from an IV set.

Similar to the syringe adapter 800, the syringe adapter 1200 includes a female connector 1210, a male connector 1212, and a body 1214 fluidly coupling the female connector 1210 to the male connector 1212. In some aspects, the female connector 1210 is a female Luer connector and the male connector 1212 is a male Luer connector. The syringe adapter 1200 includes a passage 1216 extending radially through the body 1214. A flexible tubing 1218 is fluidly coupled to an end of the passage 1216 that is exterior to the body 1214. The flexible tubing 1218 is also fluidly coupled to a filter housing 1220. The filter housing 1220 terminates at a vent 1222, which is also in fluid communication with the flexible tubing 1218. A filter 1224 is disposed in the filter housing 1220 between the vent 1222 and the flexible tubing 1218 and filters ambient air entering the vent 1222 to the flexible tubing 1218. In some aspects, a cap 1225 is hingedly coupled to the filter housing 1220 to secure the filter 1224 within the filter housing 1220 and facilitate in replacement of the filter 1224.

The syringe adapter 1200 also include a cannula 1226 fluidly coupled to the passage 1216 at an end of the passage 1216 that is disposed within the body 1214. The cannula 1226 extends axially within the body 1214 and out through the female connector 1210. An opening 1228 of the cannula 1226 is arranged axially offset from, and exterior to, the female connector 1210. A first fluid path is formed through, at least, the cannula 1226, the passage 1216, the flexible tubing 1218, and the vent 1222. A second fluid path is formed through, at least, the female connector 1210, the body 1214, and the male connector 1212.

The syringe adapter 1200 is configured to couple with a fluid source, such as, for example, the syringe 110 and includes a clip 1230 for securing the flexible tubing 1218 in place against the syringe barrel 116 of the syringe 110 when the syringe adapter 1200 is coupled to the syringe 110. In some aspects, the clip 1230 includes an annular shape with a slit 1232 to facilitate the placement of the clip 1230 around the syringe barrel 116 and the flexible tubing 1218 for holding the flexible tubing 1218 to the syringe barrel 116. For example, when the syringe adapter 1200 is coupled to the syringe 110, the flexible tubing 1218 is arranged axially along the syringe barrel 116, such that the clip 1230 is arranged around the syringe barrel 116 with the filter housing 1220 proximate the collar 118 and with the flexible tubing 1218 secured against the syringe barrel 116 and arranged between the clip 1230 and the syringe barrel 116. With the filter housing 1220 arranged proximate the collar 118 and above (e.g., axially beyond) a level of any fluid in the syringe chamber 130, the filter housing is elevated with respect to the female connector 1210 and the filter 1224 is prevented from contact with fluid from the syringe chamber 130 if the plunger 122 is accidentally depressed.

The female connector 1210 is configured to couple with a male connector of a fluid source, such as, for example, the syringe 110. The male connector 1212 is configured to couple with a female connector of a medical device, such as, for example, a needle-free connector 1234, which is, in turn, coupled to the IV set 114, for example. In operation, the syringe adapter 1200 is coupled to the IV set 114 via the needle-free connector 1234 and the syringe 110 is coupled to the syringe adapter 1200, such that the opening 1228 of the cannula 1226 is arranged within the syringe chamber 130 of the syringe 110. As the first fluid path provides filter ambient air into the syringe chamber 130, a reservoir is created in the syringe chamber 130 allowing the fluid in the syringe chamber 130 to vent through the second fluid path without requiring the plunger 122 to be depressed. Further, the filter 1224 is prevented from contact with fluid from the syringe chamber 130 in scenarios when the plunger 122 is accidentally depressed because the filter housing 1220 and the filter 1224 is raised above the level of any fluid in the syringe chamber 130. In some aspects, the fluid in the syringe chamber 130 flows through the second fluid path by gravity. In other aspects in which the IV set 114 includes the pumping segment 140, a bag pump (not shown) is utilized, such that the pumping segment 140 is inserted into the bag pump to regulate peristaltic manipulation causing the fluid to flow through the second fluid path.

Figure 16:
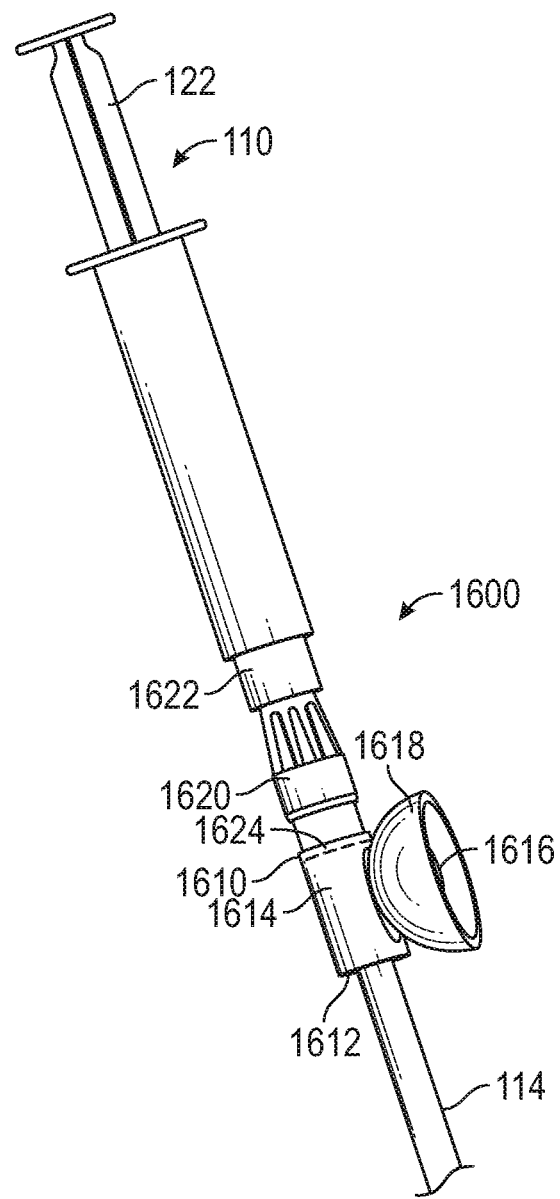
FIG. 16 illustrates a perspective view of another alternative embodiment of a syringe adapter depicting a container in a pre-filled state, in accordance with aspects of the present disclosure.
Figure 17:
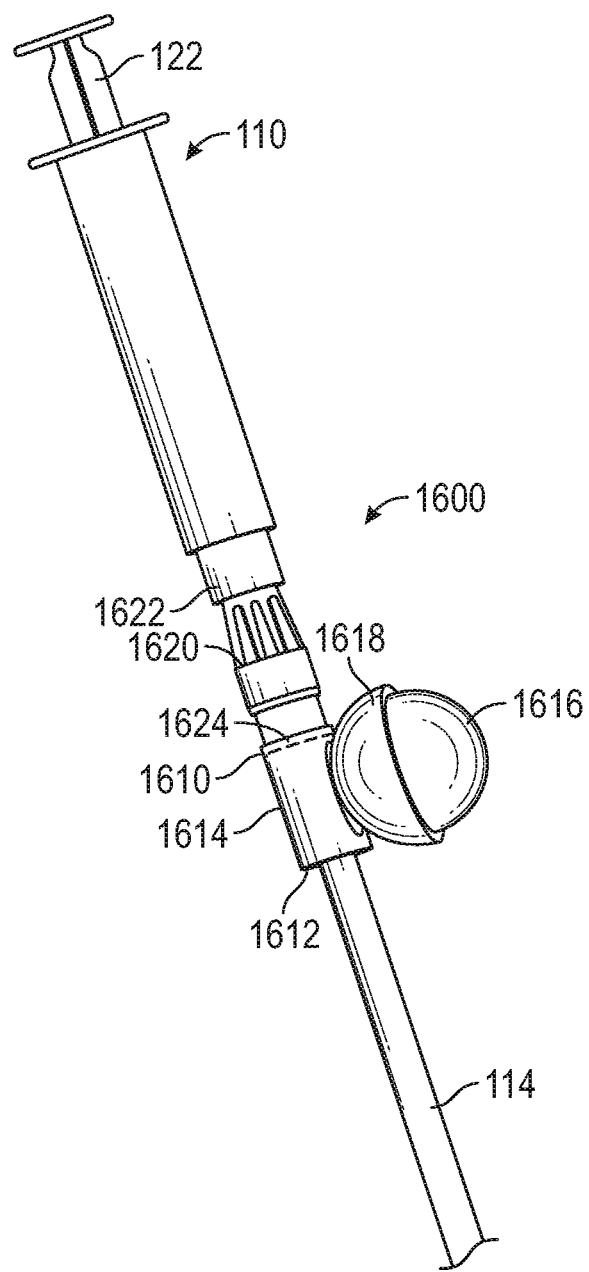
FIG. 17 illustrates a perspective view of the syringe adapter of FIG. 16 depicting the container in a filled state, in accordance with aspects of the present disclosure.

FIGS. 16 and 17 illustrate another embodiment syringe adapter 1600. The syringe adapter 1600 also provides a closed system during a fluid source change from an IV set. The syringe adapter 1600 includes a female connector 1610, a male connector 1612, and a body 1614 fluidly coupling the female connector 1610 to the male connector 1612. In some aspects, the female connector 1610 is a female Luer connector and the male connector 1612 is a male Luer connector. The syringe adapter 1600 includes a chamber 1616 fluidly coupled to, and extending outwardly from, the body 1614. The chamber 1616 can be, for example, a resilient bag, a non-resilient bag, or a collapsible plastic container. In some aspects, the syringe adapter 1600 includes a holder 1618 for supporting the chamber 1616. The syringe adapter 1600 also includes a needle-free connector 1620 disposed at, and in fluid communication with, the female connector 1610. In some aspects, the needle-free connector 1620 integrally formed with the female connector 1610. In some other aspects, the needle-free connector 1620 includes a male connector, which is couplable to the female connector 1610. The needle-free connector 1620 also includes a female fitting 1622, which is couplable to a male connector of a medical device, such as the syringe 110. A valve 1624 (shown in phantom), such as a check valve, for example, is disposed between the needle-free connector 1620 and the female connector 1610. The valve 1624 is configured to allow fluid flow from the needle-free connector 1620 to the female connector 1610 and prevent fluid flow from the female connector 1610 to the needle-free connector 1620.

In operation, the male connector 1612 of the syringe adapter 1600 is coupled to a medical device, such as, for example, a pump fitting or the connector 134 of the IV set 114. With the syringe adapter 1600 coupled to the medical device, the syringe 110 is then coupled to the needle-free connector 1620 of the syringe adapter 1600. The plunger 122 of the syringe 110 is depressed to push the fluid in the syringe 110 through the needle-free connector 1620, the female connector 1610, and into the chamber 1616. For example, in aspects where the chamber 1616 is a resilient elastomeric bag, the chamber 1616 is unfilled with fluid, as illustrated in FIG. 16, and is inflated and filled with fluid, as illustrated in FIG. 17. With the fluid emptied from the syringe 110 and filled in the chamber 1616, the syringe 110 can be uncoupled from the syringe adapter 1600 to provide a closed system via the needle-free connector 1620. Fluid in the chamber 1616 can then subsequently flow through the male connector 1612 to the IV set 114 either by gravity or via a pump (not shown) as atmospheric pressure allows the fluid in the chamber 1616 to flow without resistance. When additional medication is required the needle-free connector 1620 can be swabbed and a new syringe coupled to the needle-free connector 1620 to fill the chamber 1616 as described above.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A syringe adapter for coupling with a syringe, the syringe adapter comprising:
   a housing;
   a needle-free connector disposed in the housing;
   a communication member in slidable engagement with the housing, the communication member slidable, with respect to the housing, between an unactuated state and a coupled, actuated state of the syringe adapter;

a cannula extending from the communication member, wherein, in the unactuated state, the cannula is retracted within the needle-free connector and, in the coupled, actuated state, the cannula protrudes through and axially beyond the needle-free connector; and a piston element disposed in the needle-free connector, the piston element comprising a piston head and a sealable orifice disposed through the piston head, wherein the sealable orifice is in a sealed state when the piston element is in an uncompressed state and is in an opened state when the piston element is in a compressed state, wherein the needle-free connector comprises a connection port sealingly flush with the piston head and the sealable orifice when the syringe adapter is uncoupled with the syringe.

2. The syringe adapter of claim 1, further comprising a conduit extending from, and disposed through, the communication member, wherein the conduit is fluidly separated from the needle-free connector when the syringe adapter is coupled with the syringe and in the unactuated state.

3. The syringe adapter of claim 2, wherein the conduit is in fluid communication with the needle-free connector when the syringe adapter is coupled with the syringe and in the actuated state.

4. The syringe adapter of claim 3, further comprising a duct extending from, and through, the communication member, wherein the duct fluidly couples the cannula to at least one vent disposed in a filter housing.

5. The syringe adapter of claim 4, further comprising a filter disposed in the filter housing and a valve disposed between the filter and the cannula, wherein the valve is configured to allow fluid to flow from the at least one vent through the filter to the cannula and is configured to prevent fluid flow from the cannula to the filter.

6. The syringe adapter of claim 5, further comprising a first fluid path and a second fluid path when the syringe adapter is coupled to the syringe and in the actuated state.

7. The syringe adapter of claim 6, wherein the first fluid path is configured to provide filtered ambient air into the syringe and the second fluid path is configured to allow fluid from the syringe to flow to an intravenous set coupled to the syringe adapter.

8. The syringe adapter of claim 7, wherein the first fluid path flows through at least the cannula, the duct, and the at least one vent.

9. The syringe adapter of claim 6, wherein the second fluid path flows through at least the connection port, the piston element, and the conduit.

* * * * *